United States Patent
Chu

(10) Patent No.: US 11,083,766 B2
(45) Date of Patent: Aug. 10, 2021

(54) USES OF SOYBEAN SEED EXTRACT COMPOSITION FOR ALLEVIATING CANCER PAIN AND/OR TREATING CANCER SKIN INFLAMMATION

(71) Applicant: CHARSIRE BIOTECHNOLOGY CORP., Tainan (TW)

(72) Inventor: I-Hung Chu, Tainan (TW)

(73) Assignee: CHARSIRE BIOTECHNOLOGY CORP., Tainan (TW)

( * ) Notice: Subject to any disclaimer, the term of this patent is extended or adjusted under 35 U.S.C. 154(b) by 137 days.

(21) Appl. No.: 16/403,957

(22) Filed: May 6, 2019

(65) Prior Publication Data

US 2020/0353026 A1    Nov. 12, 2020

(51) Int. Cl.
| | | |
|---|---|---|
| *A61K 36/48* | (2006.01) | |
| *A61K 36/185* | (2006.01) | |
| *A61P 29/00* | (2006.01) | |
| *A61P 35/00* | (2006.01) | |
| *A61K 9/00* | (2006.01) | |

(52) U.S. Cl.
CPC .......... *A61K 36/185* (2013.01); *A61K 9/0014* (2013.01); *A61P 29/00* (2018.01); *A61P 35/00* (2018.01); *A61K 2236/33* (2013.01); *A61K 2236/37* (2013.01); *A61K 2236/51* (2013.01)

(58) Field of Classification Search
None
See application file for complete search history.

(56) References Cited

U.S. PATENT DOCUMENTS

| | | | | |
|---|---|---|---|---|
| 2005/0037098 A1* | 2/2005 | Chu | ..................... | A61K 8/9789 424/757 |
| 2015/0104485 A1* | 4/2015 | Garcia Anton | .......... | A61K 9/06 424/401 |
| 2017/0348370 A1* | 12/2017 | I-Hung | ................. | A61K 36/48 |

FOREIGN PATENT DOCUMENTS

| | | |
|---|---|---|
| AU | 2005203059 | 2/2006 |
| CN | 102379917 B | 4/2014 |
| JP | 4-139132 | 5/1992 |
| JP | 2001-97842 | 4/2001 |
| TW | 1610318 B | 11/2018 |

OTHER PUBLICATIONS

Georgetti et al. (2006) Eur. J. Pharma.-Biopharmaceuticals 64: 99-106. (Year: 2006).*
Waqas et al. (2015) Acta Poloniae Pharmacetica—Drug Research vol. 72, No. 1, pp. 3-11. (Year: 2015).*
Taiwan (R.O.C.) Office Action and Search Report dated Dec. 5, 2019.
Search Report dated Oct. 17, 2019 for corresponding European Patent Application No. 19172844.3.
CN 102379917 B _ Espacenet English Translation.
Ming-Yii Huang, et al. "The Reduction Effect of Extracts of Soybean Seeds on Acute Radiation Dermatitis" Fooyin J Health Sci 2010; 2(1): 21-25.
Meng-Chien Hsieh et al.: "A Single-Center, Randomized: Double-Blind, Placebo-Controlled China Trial of the Effectiveness of ANTI Soybean Extract Cream on Skin Recovery After Nd:YAG Laser Treatment": Annals of Plastic Surgery: vol. 80, Supplement 1: Feb. 2018: pp. 26-29: XP055621469: US: ISSN: 0148-7043, DOI:10.1097/SAP.0000000000001.287 *the whole document*.
Anonymous: 11 Canter Adjuvant Therapy New Drug ANTI: Nov. 24, 2018 (Nov. 24, 2018), XP055621472: Retrieved from the Internet: URL:https://web.archive.org/web/2018112419032/http://charsire.com.tw/en/??????antl/ [retrieved on Sep. 12, 2019] *the whole document*.
Herman Adlerereutz: Phyto-oestrogens and cancer: The Lancet Oncology: vol. 3 Jun. 2002: pp. 364-373.
W. Lu Lee-Jane, et al.: Effects of Soya Consumption for One Month on Steroid Hormones in Premenopausal Women: Implications for Breast Cancer Risk Reduction: Cancer Epidemiology, Biomarkers & Prevention: vol. 5, 63-70: Jan. 1966.
Oksanta A. Matvienko, el al.: A. single daily dose of soybean phytosterols in ground beef decreases serum total cholesterol and LDL cholesterol in young, mildly hypercholestero-lemic men[1-4], Am J Clin Nutr: 2002: pp. 76:57-64: American Society for Clinical Nutrition.
Yashuhlro Takahata, et al.: Highly Polymerized Procyanidins in Brown Soybean Seed Coat with a High Radical-Scavenging Activity: J. Agric. Food Chem.: vol. 49: No. 12: 2001 pp. 5841-5847.
Yukiko Minamiyama, el al.: Anlioxidatiye Effects of a Processed Grain Food: J. Nutr. Sci. Vitaminol: vol. 40: No. 5: 467-477: 1994.
Wu S. J. et al.: Evaluation of hepatoprotective activity: Phytomedicine, vol. 8(3), pp. 213-219.

* cited by examiner

*Primary Examiner* — Russell G Fiebig
(74) *Attorney, Agent, or Firm* — Ladas & Parry LLP

(57) ABSTRACT

The disclosure relates to a method for alleviating cancer pain and/or treating cancer skin inflammation in a subject in need of such treatment; the soybean seed extract composition comprises a soybean seed extract and a soybean seed vapor fraction.

11 Claims, 11 Drawing Sheets

USES OF SOYBEAN SEED EXTRACT COMPOSITION FOR ALLEVIATING CANCER PAIN AND/OR TREATING CANCER SKIN INFLAMMATION

FIELD OF TUE INVENTION

The disclosure relates to novel pharmaceutical use of a soybean seeds extract.

BACKGROUND OF THE INVENTION

*Glycine max* (L.) Merr., including soybean and black soybean, is one of the most important sources of oil and proteins in the world. For instance, soybeans can be processed to obtain edible oil that is used as salad oil, or for manufacture of margarine and shortening. Soybean oil can be also used in the manufacture of paints, linoleum, oilcloth, printing inks, soaps, insecticides, and disinfectants. Besides, lecithin phospholipids obtained from the by-products of the oil industry, can be used as wetting and stabilizing agents in food, cosmetics, pharmaceuticals, leathers, paints, plastics, soaps, and detergents. Soy meal is a very protein-rich feeding stuff for livestock. In addition, soybean protein can be used in manufacture of synthetic fibers, adhesives, textile sizing, waterproofing, fire-fighting foams and so on.

In medical use, soybeans have been reported to have effects on many diseases.

Soybean can be used as a nutritious supplement for regulating the functions of bowels, heart, kidney, liver, and stomach. Since soybean oil contains a high amount of unsaturated fatty acids, it can be used to combat hypercholesteremia. Medical lecithin from soybeans functions as a lipotropic agent. In addition, tigmasterol known as an anti-stiffness factor, and sitosterol used as a replacement for diosgenin some antihypertensive drugs, are prepared from soybeans. Isoflavones and phyto-oesterogens found in soybeans have been suggested to have a preventive effect against various cancers comprising breast, prostate, and colon cancers (Adlercreutz, H.; Phyto-oestrogens and cancer. The Lancet Oncology, 2002. Vol. 3, p. 364-373). Other literature indicates that in order to achieve the effect on preventing the occurrence of breast cancer of isoflavones, at least 100 mg daily dose should be consumed continually for a month, and it represents that only by being, consumed continually at the high dose, isoflavones exhibit anti-cancer effect (Lu Li, Anderson K E, Grady J J, Nagamani M.; Effects of soya consumption for one month on steroid hormones in premenopausal women: implications for breast cancer risk reduction. Cancer Epidemiol Biomarkers Prev. 1996 Jan. 5 (1): 6370). Consumption of phytosterol-supplemented margarine is also found to lower total plasma cholesterol and LDL-cholesterol concentrations in older middle-aged hypercholesterolemic individuals (MaNienko O. A., Lewis, D. S., Swanson, M., Aendt, B., Rainwater, D. L., Stewart, and Alekel, D. L.; A single daily dose of soybean phytosterols in ground beef decreases serum total cholesterol and LDL, cholesterol in young, mildly hypercholesterolemic men. Am J Clin Nutr., 2002, 76, p. 57 64).

Some extracts from soybean have been also reported to have pharmaceutical effects. 1,1-diphenyl-2-picrylhydrazyl (DPPH) radical-scavenging activity of 70% aqueous acetone extract from the seed coat of a brown soybean variety, Akita-Zairai, is disclosed (Takahata, Y., O.-Kameyama, M., Farina, S., Takahashi, M., and Suda, I.; Highly polymerized procyanidins in brown soybean seed coat with a high radical-scavenging activity. J. Agric. Food Chem., 2001, 49, p. 5843 5847). An extract from germ extracts, soybean, rice bran, tear grass, sesame, wheat, citron, green tea, green leaf extract, and malted rice, which are slowly roasted under a temperature at less than 60° C. and fermented with *Aspergillus oryzae* over 3 days to transform each ingredient into low molecular weight substances, is found to have antioxidative effects (Minamiyama, Y., Yoshikawa, T. Tanigawa, T., Takahashi, S., Naito, Y. Ichikawa, H., and Kondo, M.; Antioxidative effects of a processed grain food. J. Nutr. Sci. Vitaminol. 1994, 40, p. 467 477). Water extract of black soybean is also reported to effect on acetaminophen-induced liver injury by measuring serum glutamate-oxalate-transaminase (sGOT) and serum glutamate-pyruvate-transaminase (sGPT) activities in rats (Wu, S.-J., Wang, J.-S. and Chang, C.-H.; Evaluation of hepatoprotective activity of legumes. Phytomedicine, 2001, Vol. 8 (3), p. 213 219).

Some specific extracts from soybean have been found to be applied in cosmetics or pharmaceuticals in treating some skin diseases. A soya extract, which contains sphingomyelins and phospholipids in defined ratios is disclosed to be used in cosmetics for the treatment of dry skin (U.S. Patent Pub. No. US2002/0009509 A1). Such extract is produced by extracting ripe whole soya beans or oil-free soya flour using aliphatic alcohols alone or in a mixture with water and followed by the treatment with aliphatic hydrocarbons and with aliphatic ketones. Therefore, the extract is liposoluble.

An acne medicine, cosmetic production inhibitor or cosmetic composition containing one or more plant extracts selected from whey, and a Phellodendeon amurense Ruprecht extract, and further one or more extracts selected from Scutellaria baicalensis Geoegi, Symphytum officinale Linne, and *Glycine max* (L.) Merrill, is found to be effective on preventing or treating skin diseases such as acne or inflammatory chapped skin caused by the acne (JP Patent No. 2001097842).

Products of fermenting soybean by microorganisms are also applied as anti-active oxygen action compositions, agents, foods, cosmetics and medicines (such as JP Patent No. 4139132).

Although many uses of soybeans have been reported, different applications of soybean extract are vet to be developed.

SUMMARY OF THE INVENTION

The disclosure relates to use of a soybean seeds extract for alleviating cancer pain and/or treating cancer skin inflammation.

The disclosure is to provide a method for alleviating cancer pain and/or treating cancer skin inflammation in a subject in need of such treatment comprising administrating said subject pharmaceutically effective amount of a soybean extract composition and optional pharmaceutically acceptable carrier or excipient, wherein the soybean extract composition comprises a soybean seed extract and a soybean vapor fraction, which soybean seed extract s prepared by a process comp sing steps of (a) providing soybean seeds and an extracting solution, which extracting solution is water or an alcohol solution containing alcohol at the concentration lower than about 90 wt %;

(b) extracting the soybean seeds with the extracting solution at a barometric pressure lower than or equal to about 101.325 kPa and at a temperature lower than about 60° C. to obtain a crude extract; and (c) removing solids from the crude extract to obtain a liquid portion;

which soybean seed vapor fraction is prepared by a process comprising steps of:
(i) providing soybean seeds in a second extracting solution, which second extracting solution is water or an alcohol solution containing alcohol at the concentration lower than about 15 wt %; and
(ii) extracting the soybean seeds with the second extracting solution at a barometric pressure lower than about 101.325 kPa and at a temperature lower than about 110° C. and collecting the vapor fraction.

The disclosure is to provide a soybean extract composition and optional pharmaceutically acceptable carrier or excipient for use in alleviating cancer pain and/or treating cancer skin inflammation, wherein the soybean extract composition comprises a soybean seed extract and a soybean vapor fraction, which soybean seed extract is prepared by a process comprising steps of:
(a) providing soybean seeds and an extracting solution, which extracting solution is water or an alcohol solution containing alcohol at the concentration lower than about 90 wt %;
(b) extracting the soybean seeds with the extracting solution at a barometric pressure lower than or equal to about 101.325 kPa and at a temperature lower than about 60° C. to obtain an crude extract; and
(c) removing solids from the crude extract to obtain as liquid portion;

which soybean seed vapor fraction is prepared by a process comprising steps of:
(i) providing soybean seeds in a second extracting solution, which second extracting solution is water or an alcohol solution containing alcohol at the concentration lower than about 15 wt %; and
(ii) extracting the soybean seeds with the second extracting solution at a barometric pressure lower than about 101.325 kPa and at a temperature lower than about 110° C. and collecting the vapor fraction.

The present disclosure is described in detail in the following sections. Other characteristics, purposes and advantages of the present invention can be found in the detailed description and claims.

DETAILED DESCRIPTION OF THE INVENTION

Figure 1:
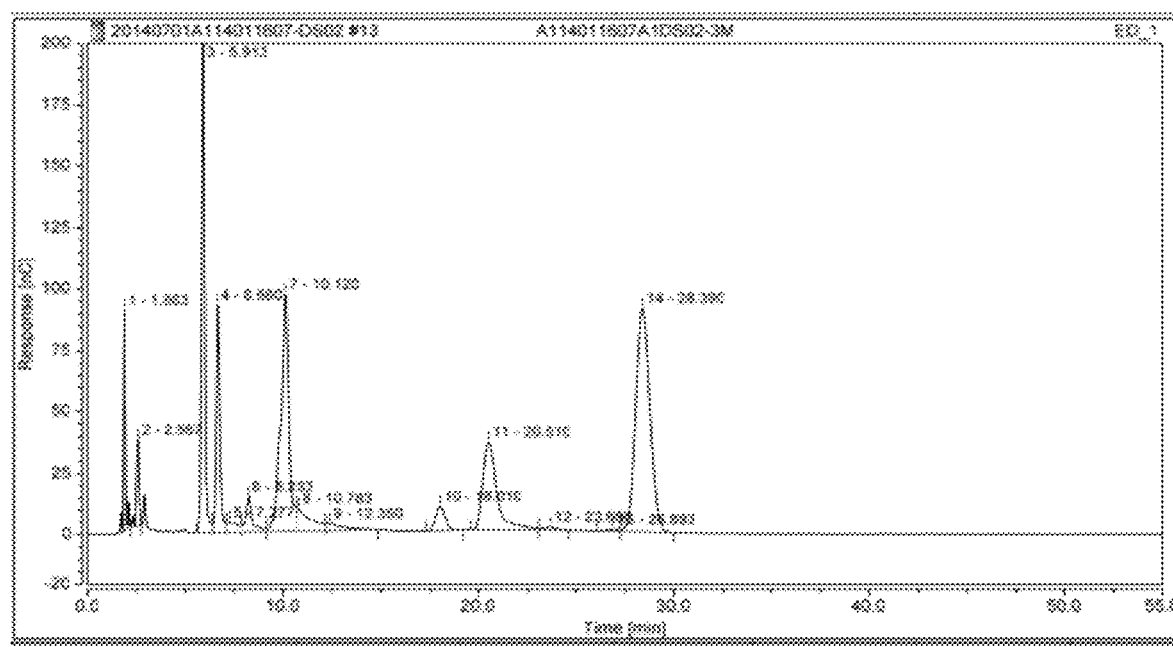
FIGS. 1 to 3 show the ion chromatography spectrograms of the soybean seed extract (GMA1) according to the disclosure.

The disclosure is to provide a method for alleviating cancer pain and/or treating cancer skin inflammation in a subject in need of such treatment comprising administrating said subject pharmaceutically effective amount of a soybean extract composition and optional pharmaceutically acceptable carrier or excipient, wherein the soybean extract composition comprises a soybean seed extract and a soybean vapor fraction, which soybean seed extract is prepared by a process comprising steps of:
(a) providing soybean seeds and an extracting solution, which extracting solution is water or an alcohol solution containing alcohol at the concentration lower than about 90 wt %;
(b) extracting the soybean seeds with the extracting solution at a barometric pressure lower than or equal to about 101.325 kPa and at a temperature lower than about 60° C. to obtain a crude extract; and
(c) removing solids from the crude extract to obtain a liquid portion;

which soybean seed vapor fraction is prepared by a process comprising steps of:
(i) providing soybean seeds in a second extracting solution, which second extracting solution is water or an alcohol solution containing alcohol at the concentration lower than about 15 wt %; and
(ii) extracting the soybean seeds with the second extracting solution at a barometric pressure lower than about 101.325 kPa and at a temperature lower than about 110° C. and collecting the vapor fraction.

The disclosure is to provide a soybean extract composition and optional pharmaceutically acceptable carrier or excipient for use in alleviating cancer pain and/or treating cancer skin inflammation, wherein the soybean extract composition comprises a soybean seed extract and a soybean vapor fraction, which soybean seed extract is prepared by a process comprising steps of:
(a) providing soybean seeds and an extracting solution, which extracting solution is water or an alcohol solution containing alcohol at the concentration lower than about 90 wt %;
(b) extracting the soybean seeds with the extracting solution at a barometric pressure lower than or equal to about 101.325 kPa and at a temperature lower than about 60° C. to obtain an crude extract; and
(c) removing solids from the crude extract to obtain a liquid portion;

which soybean seed vapor fraction is prepared by a process comprising steps of:
(i) providing soybean seeds in a second extracting solution, which second extracting solution is water or an alcohol solution containing alcohol at the concentration lower than about 15 wt %; and
(ii) extracting the soybean seeds with the second extracting solution at a barometric pressure lower than about 101.325 kPa and at a temperature lower than about 110° C. and collecting the vapor fraction.

The present disclosure can be more readily understood by reference to the following detailed description of various embodiments of the disclosure, the examples, and the chemical drawings and tables with their relevant descriptions. It is to be understood that unless otherwise specifically indicated by the claims, the disclosure is not limited to specific preparation methods, carriers or formulations, or to particular modes of formulating the extract of the disclosure into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder, disease or condition to which such term applies, or one or more symptoms of such disorder, disease or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate huller, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The soybean extract composition according to the disclosure comprises the soybean seed extract. According to the present disclosure, depending on the testa color of the seeds, the soybean may be referred to yellow soybean, vegetable soybean, white soybean, peel beans, green bean, black soybean; preferably yellow soybean or black soybean. The soybean according to the disclosure belongs to Fabaceae family, *Glycine* genus; preferably, the soybean is *Glycine max* (L.) Merrill, *Glycine formosana* Hosokawa or *Glycine soja auct.* non Sieb. & Zucc.

The soybean seed according to the disclosure preferably refers to the seed obtained by removing a shell from a pod. Generally, a soybean fruit is the pod with hair, and the shell of the pod covers the seeds. The shell of the pod is very hard and waterproof for protecting the seeds inside. The manner of obtaining the soybean seeds from the soybean fruit, i.e. removing the shell of the pod, is known by artisans skilled in this field. Preferably, the soybean seed according to the disclosure comprises seed coat, cotyledon and hypocotyl.

The soybean seed extract according to the disclosure is prepared by a process comprising steps of:
  (a) providing soybean seeds and an extracting solution, which extracting solution is water or an alcohol solution containing alcohol at the concentration lower than about 90 wt %;
  (b) extracting the soybean seeds with the extracting solution at a barometric pressure lower than or equal to about 101.325 kPa and at a temperature lower than about 60° C. to obtain a crude extract; and
  (c) removing solids from the crude extract to obtain a liquid portion.

The extracting solution for extracting the soybean seeds according to the disclosure is water or an alcohol solution containing alcohol at the concentration lower than about 90 wt %. Preferably, the alcohol is C1 to C7 alcohol. The tem "C1 to C7 alcohol" as used herein refers to linear or branched, substituted or unsubstituted, mono- or poly-functional, and saturated or unsaturated alcohol; preferably unsubstituted, mono-functional and saturated alcohol. In one preferred embodiment of the disclosure, the C1 to C7 alcohol is selected from the group consisting of methanol, ethanol, n-propanol, isopropanol, n-butanol, iso-butanol, sec-butanol, tert-butanol, 1-pentanol, 2-pentanol, 3-pentanol, 2-methyl-1-butanol, 2-methyl-2-butanol, 3-methyl-2-butanol, 3-methyl-1-butanol, 2,2-dimethyl-1-propanol, 1-hexanol, 2,4-hexadiene-1-ol, 2-methyl-cyclopentanol, cyclohexanol, 1-heptanol, 2-heptanol or cycloheptyl alcohol. More preferably, the C1 to C7 alcohol is methanol or ethanol; most preferably, the C1 to C7 alcohol is ethanol. The C1 to C7 alcohol can be used solely or in combinations.

The alcohol as used herein is preferably an alcohol solution with a concentration lower than about 90% (v/v); preferably from about 5% (v/v) to about 90% (v/v); more preferably from about 30% (v/v) to about 85% (v/v); still more preferably from about 50% (v/v) to about 75% (v/v).

The process according to the disclosure comprises (b) extracting the soybean seeds with the extracting solution at a barometric pressure lower than or equal to about 101.325 kPa and at a temperature lower than about 60° C. to obtain a crude extract. The manner of extracting a part of a seed with a solution is well-known to artisans skilled in this field. For example, the crude extract can be obtained by dividing the soybean seeds into pieces in any manner such as grinding, stirring, disturbing, cutting or shredding, and soaking the pieces in the extracting solution for extraction. The manners for dividing the seeds in the field are able to be applied in the disclosure. In one preferred embodiment of the disclosure, the soybean seeds are grinded into powder. In one preferred embodiment of the disclosure, the soybean seeds are soaked in the extracting solution for extraction; more preferably, the soybean seeds are soaked in the extracting solution and subjected to ultrasonic vibration extraction.

According to the process of the disclosure, prior to step (b), the soybean seeds are preferably dried.

According to the disclosure, the ratio (w/v) of the soybean seeds and the extracting solution is not specifically restricted. In one preferred embodiment of the disclosure, the ratio (w/v) of the soybean seeds and the extracting solution is about 1:1 to about 1:30; more preferably about 1:5 to about 1:20; and most preferably about 1:10.

The temperature of extraction in the step (b) according to the disclosure is lower than about 60° C.; preferably from about 25° C. to about 55° C.; more preferably from about 30° C. to about 50° C.; still more preferably about 45° C.

In one preferred embodiment of the disclosure, the extraction step (b) can be repeated, and the extract is collected by merging.

The process according to the disclosure comprises the step (c) removing solids from the crude extract to obtain a liquid portion. The manner of removing the solids to obtain the liquid fraction is well-known to artisans skilled in this field, and examples include but not limited to filtration, centrifugation, or precipitation.

Preferably, the process according to the disclosure further comprises a step (d) of concentrating the liquid portion obtained in the step (c) to obtain a concentrated solid portion. The manner of concentrating is well-known to artisans skilled in this field, such as by a reduced-pressure condenser.

Preferably, the process for according to the disclosure further comprises a step (e) of drying the concentrated solid portion obtained in the step (d). The manner of drying is well-known to artisans skilled in this field, such as air-drying or by a freeze drier.

In one preferred embodiment of the disclosure, the soybean seed extract is subjected to an ion chromatography assay with CarboPac PA1 Analytical (4×250 mm) column. The mobile phase is 87% water and 13% 500 mM NaOH; the internal standard is maltose monohydrate. The isocratic elution is applied with the low rate of 1.0 ml/min and the cycle of 0.5 second. In every cycle, the assay is conducted with the relative potential of 0.1 V at 0.00 second to 0.2 second; 0.1 V at 0.2 second to 0.4 second; −2.0 V at 0.41 second to 0.42 second; 0.6 V at 0.43 second; −0.1 V at 0.44 second to 0.5 second, and the total assay duration is 55 minutes.

Figure 2:
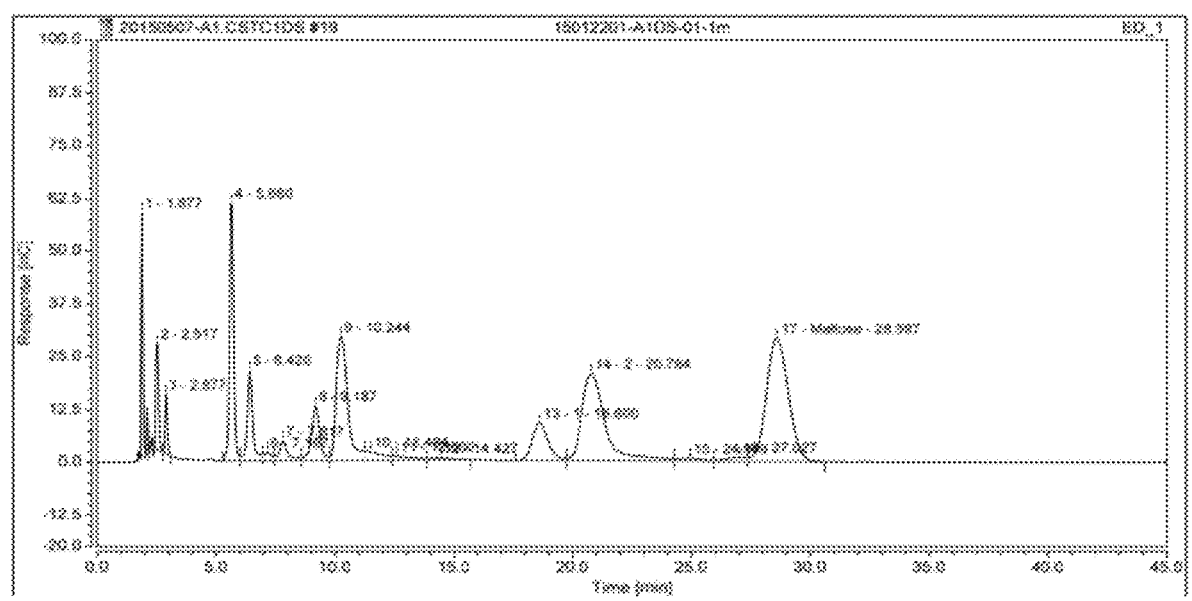
Figure 3:
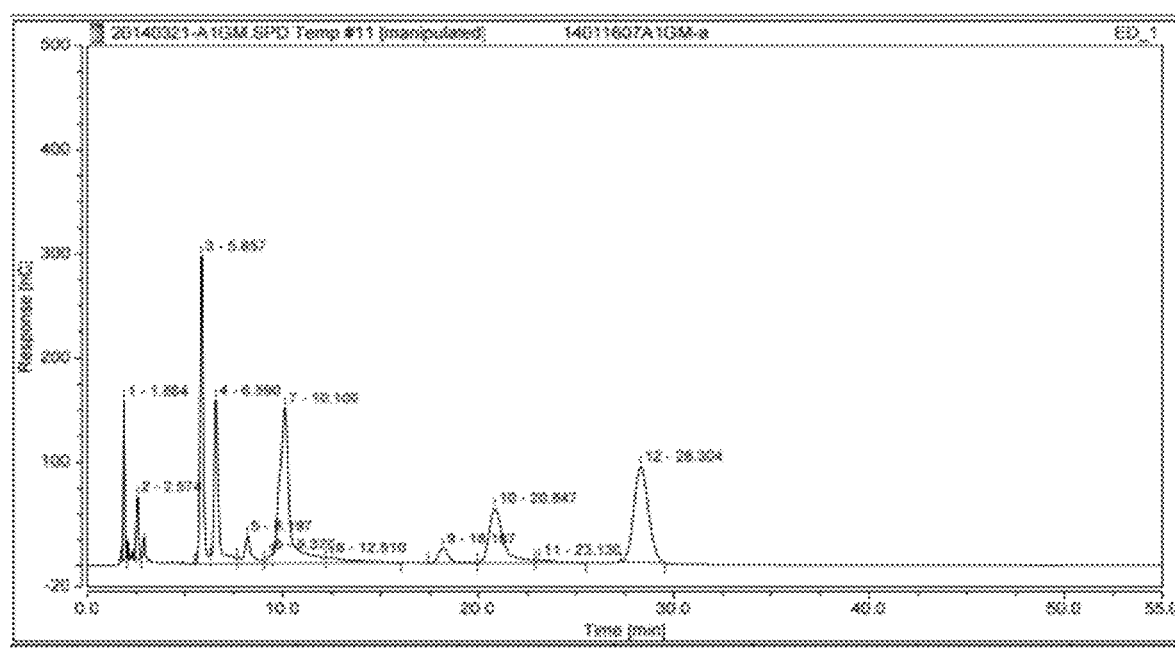

The spectrograms obtained are shown in FIGS. 1 to 3. The peak time is shown in Table 1.

TABLE 1

| | Peak time (minutes) | | | | |
|---|---|---|---|---|---|
| | Peak 1 | Peak 2 | Peak 3 | Peak 4 | Peak 5 | Internal standard |
| FIG. 1 | 5.913 | 6.660 | 10.120 | 18.010 | 20.510 | 28.390 |
| FIG. 2 | 5.660 | 6.420 | 10.244 | 18.600 | 20.784 | 28.597 |
| FIG. 3 | 5.857 | 6.590 | 10.100 | 18.167 | 20.847 | 28.304 |

Preferably, the soybean extract composition according to the disclosure further comprises a soybean seed vapor fraction, which soybean seed vapor fraction is prepared by a process comprising steps of:
  (i) providing soybean seeds in a second extracting solution, which second extracting solution is water or an alcohol solution containing alcohol at the concentration lower than about 15 wt %; and
  (ii) extracting the soybean seeds with the second extracting solution at a barometric pressure lower than about 101.325 kPa and at a temperature lower than about 110° C. and collecting the vapor fraction.

The second extracting solution for preparing the soybean seed vapor fraction according to the disclosure is water or an alcohol solution containing alcohol at the concentration lower than about 15 wt %; preferably water. The kind of the alcohol can be the same to that of the extracting solution for preparing the soybean seed extract and is not repeated herein.

The alcohol of the second extracting solution is the alcohol solution with a concentration lower than about 15% (v/v); preferably lower than about 10% (v/v); more preferably lower than about 5% (v/v).

The process for preparing the soybean seed vapor fraction according to the disclosure comprises the step (ii) extracting the soybean seeds with the second extracting solution at a barometric pressure lower than about 101.325 kPa and at a temperature lower than about 110° C. and collecting the vapor fraction. The manner of extracting can be the same to that of preparing the soybean seed extract, provided that the soybean seed vapor fraction is vaporized at a barometric pressure lower than about 101.325 kPa and at a temperature lower than about 110° C. The vapor fraction can be collected in a liquid form by chilling the vapor.

In a preferred embodiment of the disclosure, a process of vaporizing the soybean seeds at a given barometric pressure and temperature, and collecting said vapor fraction by chilling the vapor can be performed in a rotary evaporator where the vapor is evaporated to the condensing tube supplied with cold water, and then the vapor is chilled by passing through the condensing tube to collect the vapor fraction in a liquid form. The manipulation is simple and the cost is low.

According to the disclosure, the ratio (w/v) of the soybean seeds and the second extracting solution is not specifically restricted. In one preferred embodiment of the disclosure, the ratio (w/v) of the soybean seeds and the second extracting solution is about 1:1 to about 1:30; more preferably about 1:5 to about 1:20; and most preferably about 1:10.

The temperature of extraction in the step (ii) according to the disclosure is lower than about 110° C.; preferably from about 60° C. to about 110° C.

In one preferred embodiment of the disclosure, the extraction step (ii) can be repeated, and the soybean seed vapor fraction is collected by merging.

In one preferred embodiment of the disclosure, the soybean seed vapor fraction is subjected to an ion chromatography assay with CarboPac PA1 Analytical (4×250 mm) column. The mobile phase is 87% water and 13% 500 mM NaOH; the internal standard is maltose monohydrate. The isocratic elution is applied with the low rate of 1.0 ml/min and the cycle of 0.5 second. In every cycle, the assay is conducted with the relative potential of 0.1 V at 0.00 second to 0.2 second; 0.1 V at 0.2 second to 0.4 second; −2.0 V at 0.41 second to 0.42 second; 0.6 V at 0.43 second; −0.1 V at 0.44 second to 0.5 second, and the total assay duration is 55 minutes.

Figure 4:
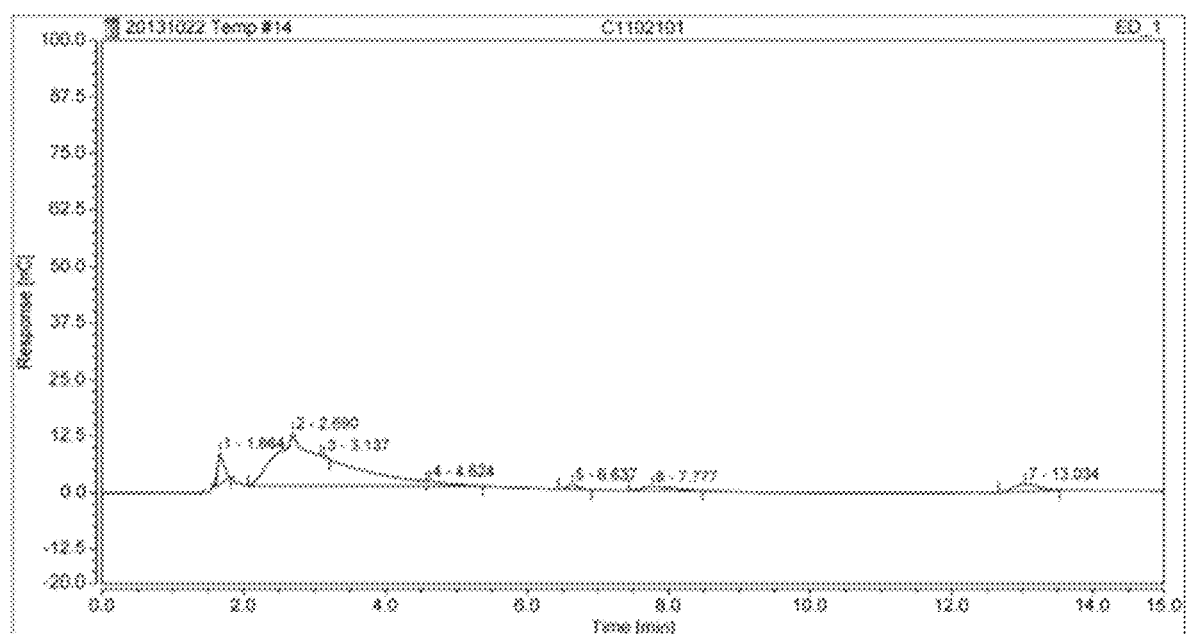
FIGS. 4 to 6 show the ion chromatography spectrograms of the soybean seed vapor fraction (GMC1) according to the disclosure.
Figure 5:
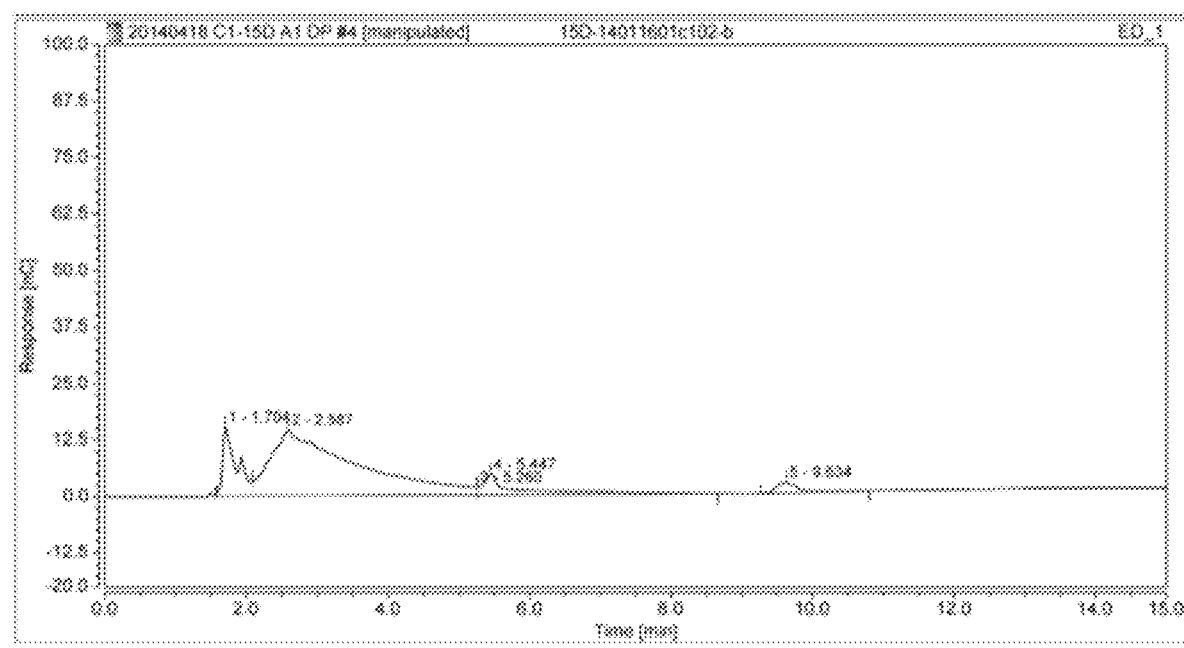
Figure 6:
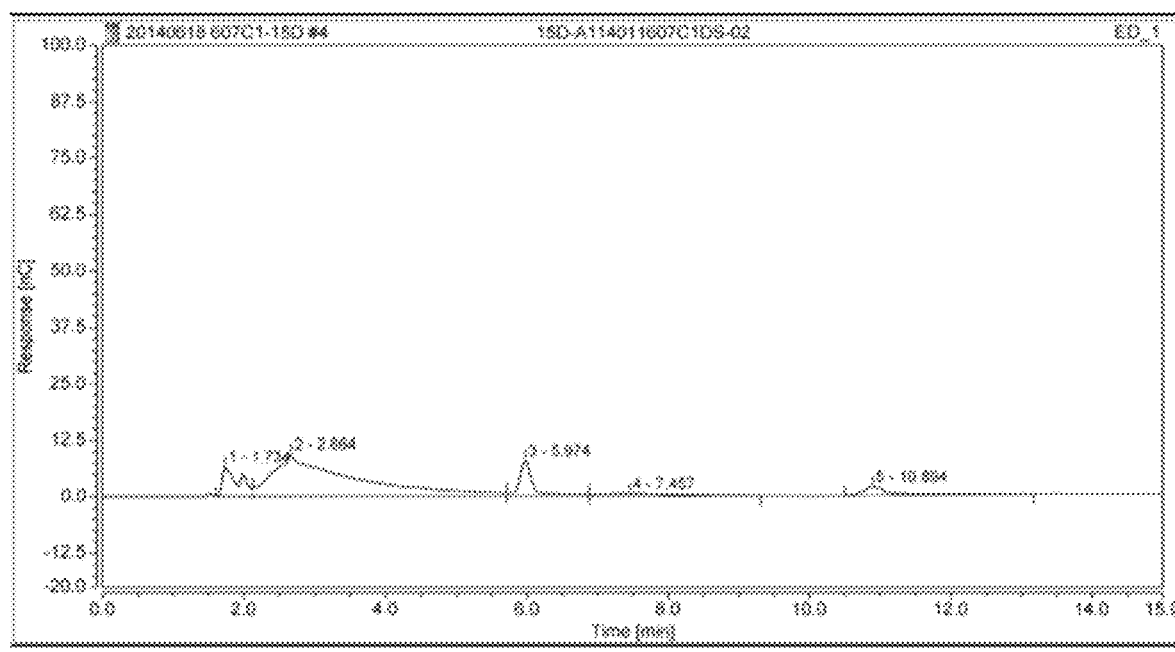

The spectrograms obtained are shown in FIGS. 4 to 6. The peak time is shown in Table 2.

TABLE 2

| | Peak time |
|---|---|
| FIG. 4 | 2.690 |
| FIG. 5 | 2.587 |
| FIG. 6 | 2.664 |

In one embodiment of the disclosure, the content of the soybean seed extraction based on the extract composition is from about 0.001% wt to about 10% wt; preferably from about 0.01% wt to about 5% wt; more preferably from about 0.001% wt to about 1.5% wt. In another aspect, the content of the soybean seed vapor fraction based on the extract composition is from about 0.04% wt to about 99.999% wt; preferably from about 10% wt to about 99.9% wt; more preferably from about 30% wt to about 99% wt.

The extraction composition according to the disclosure is preferably a pharmaceutical composition, a food composition or a cosmetic composition.

The pharmaceutical composition according to the disclosure is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present disclosure, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art.

The external route as used herein is also known as local administration, includes but is not limited to administration by insufflation and inhalation. Examples of various types of preparation for local administration include ointments, lotions, creams, gels, limns, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets err liposome microencapsulation preparations.

Ointments, creams and gels, may, for example, be formulated with an aqueous or oily base with the addition of suitable thickening and/or gelling agent and/or solvents. Such bases may thus, tar example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution. The aerosol composition may optionally contain additional formulation excipients well known in the art such as surfactants e.g. oleic acid or lecithin and cosolvents e.g. ethanol.

Topical preparations may be administered by one or more applications per day to the affected area; over the skin areas occlusive dressings may advantageously be used. Continuous or prolonged delivery may be achieved by an adhesive reservoir system.

The cosmetic composition according to the disclosure may be an aqueous phase formulation consisting essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms, such as propylene glycol, ethylene glycol, 1,3-butylene glycol or dipropylene glycol, C3-C4 ketones and C2-C4 aldehydes, and glycerin. Such an aqueous formulation preferably is in a form of aqueous gel or hydrogel formulation. The hydrogel formulation comprises a thickening agent to thicken the liquid solution. Examples of the thickening agents include, but are not limited to, carbomers, cellulose base materials, gums, algin, agar, pectins, carrageenan, gelatin, mineral or modified mineral thickeners, polyethylene glycol and polyalcohols, polyacrylamide and other polymeric thickeners. The thickening agents which give the stability and optimal flow characteristics of the composition are preferably used.

The cosmetic composition according to the present disclosure may be in a form of emulsion or cream formulation. It can contain emulsifying surfactants. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of said reference, for the anionic and nonionic surfactants.

The surfactants preferably used in the cosmetic composition according to the disclosure are chosen from: nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated fatty esters of C1-C6 alkyl glucose, and mixtures thereof; anionic surfactants: C16-C30 fatty acids neutralized with amines, aqueous ammonia or alkaline salts, and mixtures thereof. Surfactants which make it possible to obtain an oil-in-water or wax-in-water emulsion are preferably used.

The cosmetic composition according to the disclosure may further comprise an effective amount of a physiologically acceptable antioxidant selected from the group consisting of butylated p-cresol, butylated hydroquinone monomethyl ether, and a tocopherol.

The cosmetic composition according to the disclosure may further comprise natural or modified amino acid, natural or modified sterol compound, natural or modified collagen, silk protein or soy protein.

The cosmetic composition according to the disclosure is preferably formulated for topical application to keratin materials such as the skin, the hair, the eyelashes or the nails. They may be in any presentation form normally used for this type of application, especially in the form of an aqueous or oily solution, an oil-in-water or water-in-oil emulsion, a silicone emulsion, a microemulsion or nanoemulsion, an aqueous or oily gel or a liquid, pasty or solid anhydrous product.

The cosmetic composition according to the disclosure may be more or less fluid and may have the appearance of a white or colored cream, an ointment, a milk, a lotion, a serum, a paste, a mousse or a gel. It may optionally be topically applied onto the skin in the form of an aerosol, a patch or a powder. It may also be in solid form, for example, in the form of a stick. It may be used as care products and/or as makeup products for the skin. Alternatively, it may be formulated as shampoos or conditioners.

In known fashion, the cosmetic composition according to the disclosure may also contain additives and adjuvants that are common in cosmetics, such as hydrophilic or lipophilic gelling agents, preservatives, antioxidants, solvents, fragrances, fillers, pigments, odor absorbers and dyestuffs.

The extract composition can be added to a conventional food composition (i.e. the edible food or drink or precursors thereof) in the manufacturing process of the food composition. Almost all food compositions can be supplemented with the extract composition of the disclosure. The food compositions that can be supplemented with the extract composition of the disclosure include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

In one preferred embodiment of the invention, the soybean extract composition is for alleviating cancer pain caused by cancer radiation therapy and/or treating cancer skin inflammation.

The cancer according to the disclosure is preferably a solid cancer. Examples of the cancer include but are not limited to cancer of breast, face, nasopharyngeal cavity, nasal cavity, mouth, throat, tongue, brain or neck.

In one preferred embodiment of the disclosure, the soybean extract composition and optional pharmaceutically acceptable carrier or excipient is topically applied to a site of pain and/or a site of inflammation.

In one preferred embodiment of the disclosure, the pain is pain in the skin, muscles, mucous membranes, bones or glands. In one more preferred embodiment of the invention, the pain is skin inflammation pain or skin ulcers pain. In another aspect, as for sites of pain, the pain is pain in the mouth, tongue, pharynx, throat, sinuses, salivary glands, buccal, ear, external auditory canal, gums, head and neck lymph nodes or parotid glands.

The following examples are provided to aid those skilled in the art in practicing the present disclosure.

EXAMPLES

Soybean Seed Extract (GMA1)

Seeds of soybean (*Glycine max* (L.) Merr.) were grinded into power, and 70% by weight of ethanol or distilled water was applied as an extracting solution; the ratio (w/v) of the soybean seeds and the extracting solution was about 1:10. The soybean seeds were extracted at a barometric pressure about 1 atm and at a temperature of about 45° C. to obtain a crude extract. The solids were removed from the crude extract to obtain a liquid portion. The liquid portion was further concentrated by a reduced-pressure condenser to obtain a concentrated solid portion. The concentrated solid portion was further dried at 70° C.

Soybean Seed Vapor Fraction (GMC1)

Seeds of soybean (*Glycine max* (L.) Merr.) were minded into power, and 2% by weight of ethanol or distilled water was applied as a second extracting solution; the ratio (w/v) of the soybean seeds and the second extracting solution was about 1:10. The vapor fraction was obtained by vaporizing the soybean seeds in a rotary evaporator (EYELA N-1000S, 1000S-W) at a pressure of lower than 1 atm and a temperature of 90° C., and passing through a condensing tube supplied with cold water.

Analysis of the Soybean Seed Extract (GMA1) and Soybean Seed Vapor Fraction (GMC1)

The obtained soybean seed extract (GMA1) and soybean seed vapor fraction (GMC1) were subjected to an ion chromatography assay with CarboPac PA1 Analytical (4×250 mm) column. The mobile phase was 87% water and 13% 500 mM NaOH; the internal standard is maltose monohydrate. The isocratic elution was applied with the low rate of 1.0 ml/min and the cycle of 0.5 second. In every cycle, the assay was conducted with the relative potential of 0.1 V at 0.00 second to 0.2 second; 0.1 V at 0.2 second to 0.4 second; −2.0 V at 0.41 second to 0.42 second; 0.6 V at 0.43 second; −0.1 V at 0.44 second to 0.5 second, and the total assay duration was 55 minutes.

The spectrograms of the soybean seed extract (GMA1) are shown in FIGS. 1 to 3. The peak time is shown in Table 1.

The spectrograms of the soybean seed vapor fraction (GMC1) are shown in FIGS. 4 to 6. The peak time is shown in Table 2.

The Soybean Seed Extract (GMA1) Contains Very Small Amount of Isoflavones and the Soybean Seed Vapor Fraction (GMC1) Contains No Isaflavones A high performance liquid chromatography (HPLC) was applied to assay if the soybean seed extract (GMA1) and soybean seed vapor fraction (GMC1) contained isoflavones.

The condition of HPLC was listed as follows:

Apparatus: Hitachi HPLC CM5000 Series; pump: CM5110; detector: CM5430 (DAD); automatic feeding system: CM5210; column oven: CM5310; software: OpenLab.

Column: RP $C_{18}$, 4.6×250 mm 5 µm; detection wavelength: UV 254 nm; flow rate: 0.8 min/ml; column oven temperature: 30° C.; gradient: as shown in Table 3.

TABLE 3

| Time (minute) | Solvent (%) | |
| --- | --- | --- |
| | Elution 1 | Elution 2 |
| 0 | 95 | 5 |
| 10 | 85 | 15 |
| 25 | 77 | 23 |
| 35 | 72 | 28 |
| 40 | 20 | 80 |
| 45 | 20 | 80 |
| 46 | 95 | 5 |
| 55 | 95 | 5 |

Elution 1: 1% formic acid+0.01% trifluoroacetic acid (TEA) in water

Elution 2: 1% formic acid+0.01% trifluoroacetic acid in acetonitrile

Figure 7:
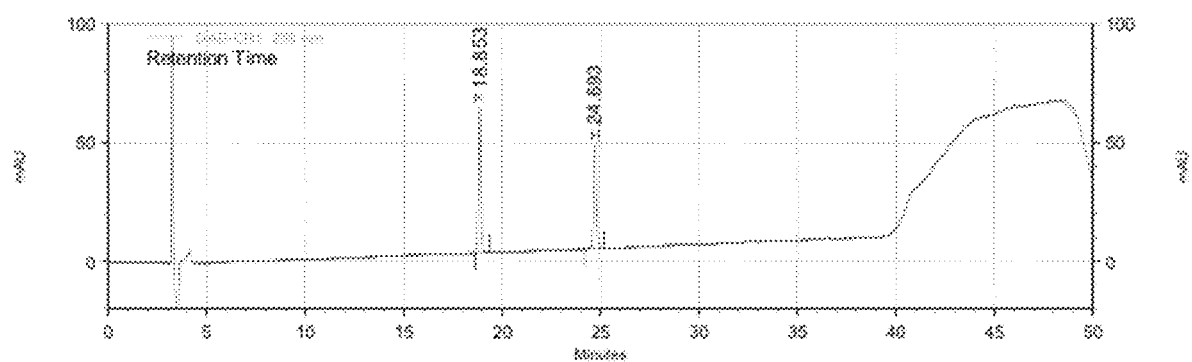
FIG. 7 shows the high performance liquid chromatography (HPLC) spectrogram of the isoflavones standard.

The HPLC spectrogram of the isoflavones standard is shown in FIG. 7, and peaks occurred at retention time of 18.853 minutes and 24.693 minutes.

Figure 8:
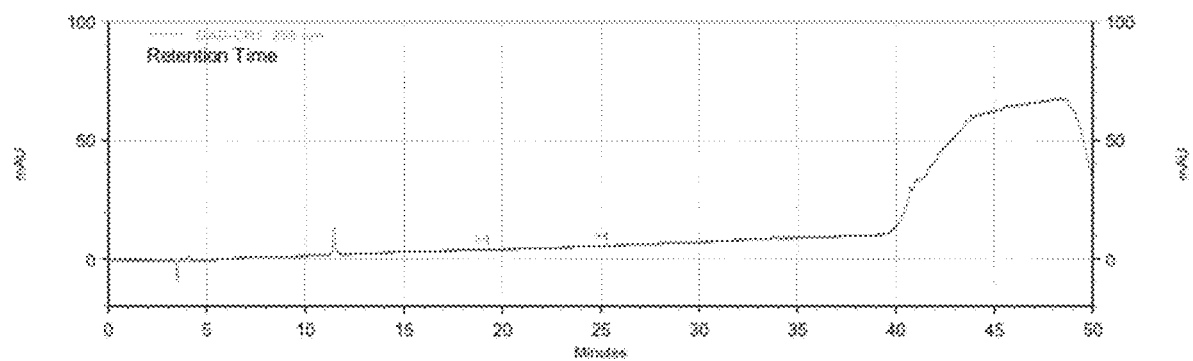
FIG. 8 shows the HPLC spectrogram of the soybean seed vapor fraction (GMC1).

The HPLC spectrogram of the soybean seed vapor fraction (GMC1) is shown in FIG. 8, and no peaks occurred.

Figure 9:
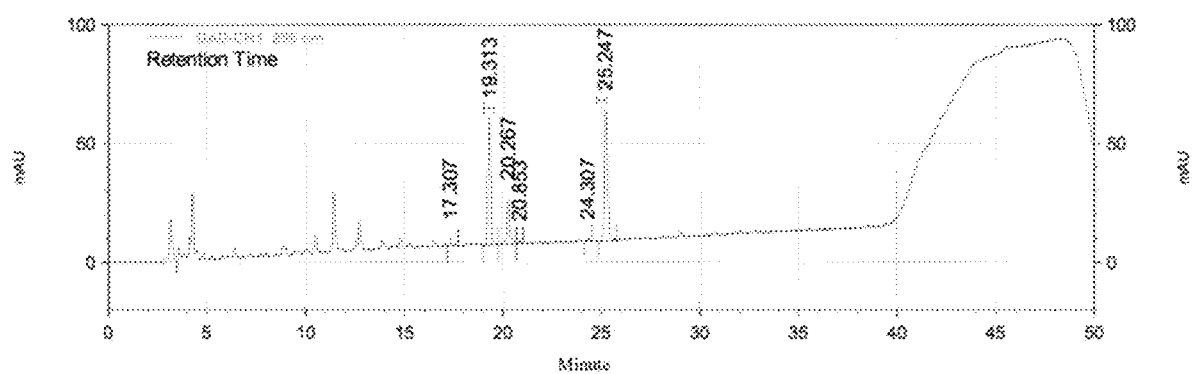
FIG. 9 shows the HPLC spectrogram of the extract composition containing 0.3 part by weight of the soybean seed extract (GMA1) and 1 part by weight of the soybean seed vapor fraction (GMC1).

The HPLC spectrogram of an ointment containing 0.3 part by weight of the soybean seed extract (GMA1) and 1 part by weight of the soybean seed vapor fraction (GMC1) is shown in FIG. 9, and peaks occurred at retention time of 17.307 minutes, 19.313 minutes, 20.267 minutes, 20.853 minutes, 24.307 minutes and 25.247 minutes.

By comparing FIGS. 7 to 9, it shows that no peaks occur in the HPLC spectrogram of the soybean seed vapor fraction (GMC1) in FIG. 8, and thus the soybean seed vapor fraction (GMC1) contains no isoflavones; the peaks corresponding to the isoflavones fingerprint absorption peaks occur at a very small amount in the HPLC spectrogram of the extract composition containing 0.3 part by weight of the soybean seed extract (GMA1) and 1 part by weight of the soybean seed vapor fraction (GMC1) in FIG. 9. After conversion, the content of daidzin is 4.8 µg/ml and the content of genistin is 8.23 µg/ml, which contents are far away from the pharmaceutically effective amount of isoflavones. Therefore, the soybean seed extract (GMA1) only contains a very small amount of isoflavones, and the pharmaceutical effect thereof is not exhibited by the very small amount of isoflavones.

Soybean Extract Composition for Alleviating Cancer Pain and/or Treating Cancer Skin Inflammation Soybean extract composition CSTC-ACA: containing 0.3 parts by weight of soybean seed extract (GMA1) and 1 part by weight of soybean seed vapor fraction (GMC1), and formulated in a cream excipient.

Subject: patients over 20 years of age diagnosed with head and neck cancer, as shown in Table 4 below.

TABLE 4

| | 28 (average) |
| --- | --- |
| Age | 56.2 years old |
| Gender | 24 males. 4 females |
| Body weight | 64.8 kg |
| Body height | 165.8 cm |
| BMI | 23.52 kg/m$^2$ |

Administration: CSTC1-ACA was applied topically to the site exposed to radiation or the site of pain twice daily for a daily dose of 30 g cream. The administration period started from 2 weeks before the radiation exposure and continued until 2 weeks after the end of the radiation irradiation.

Pain assessment: according to Brief Pain Inventory-Short Form (BPI-SF), item 9, quality of life influenced by pain was evaluated, and 6 out of 28 ended the test early.

Q1: General Activity

Q2: Mood

Q3: Walking Ability

Q4: Normal Work

Q5: Relations with other people

Q6: Sleep

Q7: Enjoyment of life

Figure 10:
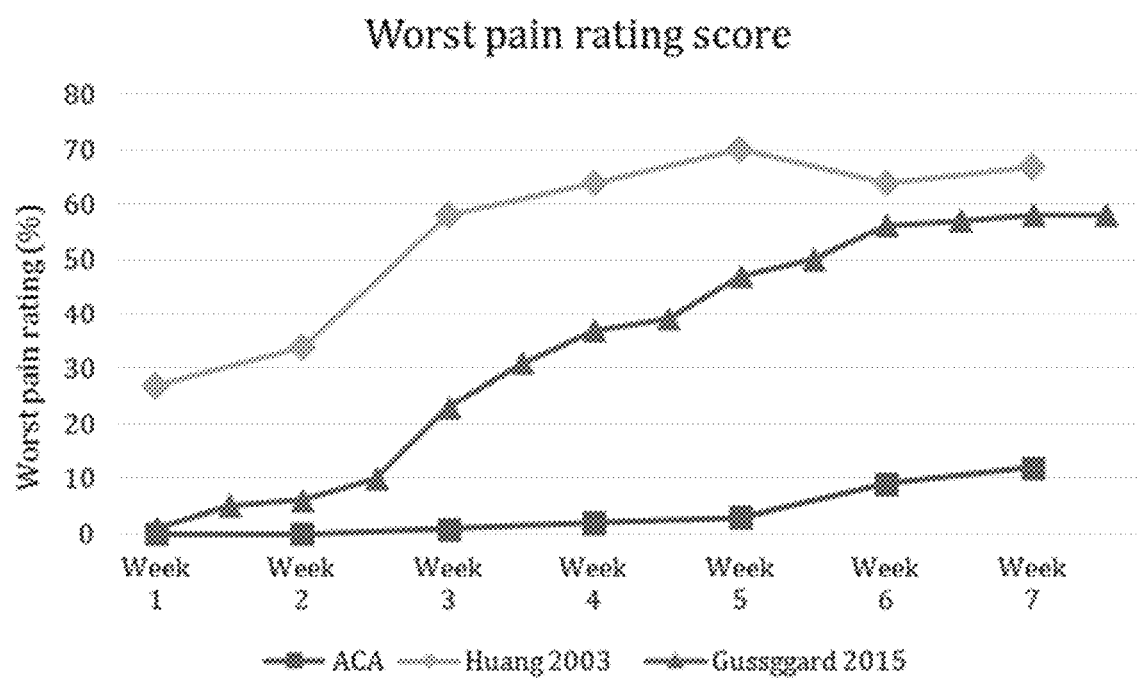
FIG. 10 shows the pattern of worst pain rating in the duration of radiotherapy.

The pattern of worst pain rating in the duration of radiotherapy is shown in FIG. 10. In FIG. 10, the results cited by Huang H Y, Wilkie D J, Chapman C R, Ting L L. Pain trajectory of Taiwanese with nasopharyngeal carcinoma over the course of radiation therapy. J Pain Symptom Manage. 2003; 25: 247-255 and Gussgard A M, Jokstad A, Wood R, Hope A J, Tenenbaum H. Symptoms Reported by Head and Neck Cancer Patients during Radiotherapy and Association with Mucosal Ulceration Site and Size: An Observational Study. PLoS One. 2015 Jun. 10; 10 (6): e0129001 are taken as control groups.

RESULTS: Subjects treated with CSTC1-ACA of the present disclosure maintained their pain at a low point during seven weeks of radiation therapy, only a slight increase in the seventh week. The time to reach the maximum pain value (days) is shown in Table 5 below.

TABLE 5

| | PP population (N = 22) |
| --- | --- |
| Censored No. | 9 (40.9%) |
| Observed No. | 13 (59.1%) |
| Q1 (95% CI) | 37 (9.0~44.0) days |
| Median (95% CI) | 54 (37.0~NA) days |
| Q3 (95% CI) | NA (56.0~NA) days |
| Mean (SE) | 48 (3.7) days |

Efficacy Note: According to the results of the above-mentioned Huang 2003 literature, the pain value began to rise at week 3 after the subjects received radiation therapy. The Gussgard 2015 literature showed that the pain reached discomfort at week 5 after the subjects received radiation therapy. Relative to the results of these two literatures, the subjects receiving the CSTC1-ACA treatment of the present disclosure (PP population) felt the worst pain at average day 48, and the subjects of the Huang 2003 and Gussgard 2015 literature felt earlier. It is apparent that CSTC1-ACA has an effect on alleviating radiation-induced pain caused by skin symptoms.

The evaluation of the inflammatory index during radiation exposure is shown in Table 6 below.

TABLE 6

| | Grade | | | |
|---|---|---|---|---|
| | 1 | 2 | 3 | 4 |
| Dermatitis | Faint erythema or dry desquamation | Moderate to obvious erythema, flaky wet desquamation (prone to skin folds), moderate edema | Moist desquamation in areas other than skin folds, bleeding induced by minor trauma | Full-thickness skin necrosis or ulceration. spontaneous bleeding, skin graft indicated death |

Figure 11:
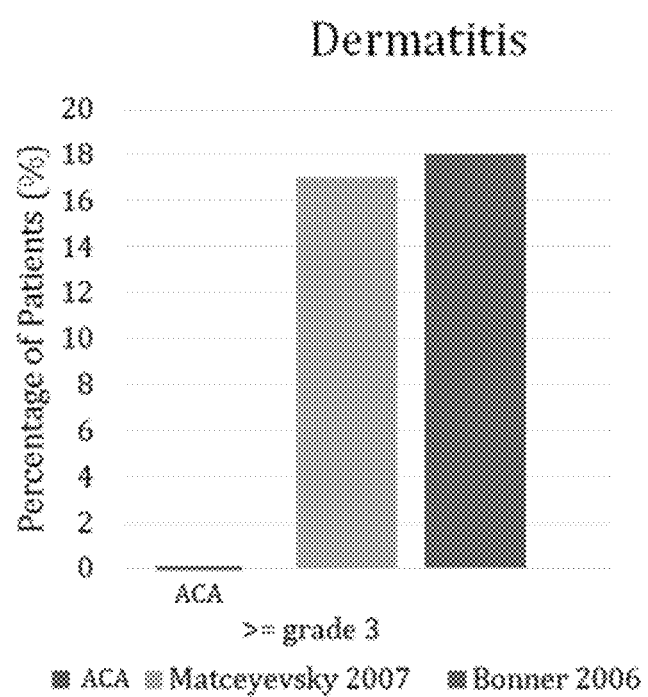
FIG. 11 shows the proportion of patients with dermatitis severity (grade 1-4, mild to severe) reaching grade 3 or higher before, during, and after cancer radiation treatment is lower than the proportion of patients in the control literatures.

The dermatitis severity at week 5 of radiation exposure is shown in FIG. 11 and Table 7.

TABLE 7

| | Grade 0 | Grade 1 | Grade 2 | Grade 3 |
|---|---|---|---|---|
| CSTC1-ACA | 27% | 73% | 0% | 0% |

According to the results of Matceyevsky D, Hahoshen N Y, Vexler A, Asna N, Khafif A, Ben-Yosef R. Assessing the Effectiveness of Dead Sea Products as Prophylactic Agents for Acute Radiochemotherapy-Induced Skin and Mucosal Toxicity in Patients with Head and Neck Cancers: A Phase 2 study. Isr Med Assoc J 2007; 9: 439-442, about 17% of the subjects had grade 3 or 4 dermatitis after radiation therapy. According to the results of Bonner J A, Harari P M, Giralt J, Azarnia N, Shin D M, Cohen R B et al. Radiotherapy plus Cetuximab for Squamous-Cell Carcinoma of the Head and Neck. new Engl J of Med 2006; 354: 567-578, about 18% of the subjects developed dermatitis above grade 3. The subjects receiving CSTC1-ACA treatment had a very low rate of dermatitis above grade 3 during radiation therapy.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for alleviating pain caused by cancer radiation therapy in a subject in need of such treatment, wherein the pain is in a muscle, mucous membrane, bone or gland of the subject, the method comprising administrating said subject pharmaceutically effective amount of a soybean extract composition and optional pharmaceutically acceptable carrier or excipient, wherein the soybean extract composition comprises a soybean seed extract and a soybean vapor fraction, which soybean seed extract is prepared by a process comprising steps of:
(a) providing soybean seeds and an extracting solution, which extracting solution is water or an alcohol solution containing alcohol at the concentration lower than about 90 wt %;
(b) extracting the soybean seeds with the extracting solution at a barometric pressure lower than or equal to about 101.325 kPa and at a temperature lower than about 60° C. to obtain a crude extract; and
(c) removing solids from the crude extract to obtain a liquid portion;

which soybean seed vapor fraction is prepared by a process comprising steps of:
(i) providing soybean seeds in a second extracting solution, which second extracting solution is water or an alcohol solution containing alcohol at the concentration lower than about 15 wt %; and
(ii) extracting the soybean seeds with the second extracting solution at a barometric pressure lower than about 101.325 kPa and at a temperature lower than about 110° C. and collecting the vapor fraction.

2. The method according to claim 1, wherein the process for preparing the soybean seed extract further comprises a step (d) of concentrating the liquid portion obtained in the step (c) to obtain a concentrated solid portion.

3. The method according to claim 2, wherein the process for preparing the soybean seed extract further comprises a step (e) of drying the concentrated solid portion obtained in the step (d).

4. The method according to claim 1, wherein the alcohol solution of the second extracting solution in step (i) contains alcohol at the concentration lower than about 5 wt %.

5. The method according to claim 4, wherein the content of the soybean seed extract is from about 0.001 wt % to about 5 wt % in the soybean extract composition; and the content of the soybean seed vapor fraction is from about 95 wt % to about 99.999 wt % in the soybean extract composition.

6. The method according to claim 1, which is for alleviating the pain caused by cancer radiation therapy and for treating cancer skin inflammation in the subject.

7. The method according to claim 1, wherein the cancer is cancer of breast, face, nasopharyngeal cavity, nasal cavity, mouth, throat, tongue, brain or neck.

8. The method according to claim 1, wherein the soybean extract composition and optional pharmaceutically acceptable carrier or excipient is topically applied to a site of the pain.

9. The method according to claim 1, wherein the pain is in the mouth, tongue, pharynx, throat, sinuses, salivary glands, buccal, ear, external auditory canal, gums, head and neck lymph nodes or parotid glands of the subject.

10. The method according to claim 1, wherein the soybean extract composition and optional pharmaceutically acceptable carrier or excipient is topically applied to a site where the subject is exposed to radiation.

11. The method according to claim 1, wherein the soybean extract composition and optional pharmaceutically acceptable carrier or excipient is topically applied to a site where the subject is exposed to radiation both before and after the exposure to radiation.

* * * * *